United States Patent
Rozsa

(10) Patent No.: US 11,123,223 B2
(45) Date of Patent: Sep. 21, 2021

(54) LOW POWER LIGHT THERAPY DEVICE FOR TREATING THE EYE

(71) Applicant: Tamas Rozsa, Budakalasz (HU)

(72) Inventor: Tamas Rozsa, Budakalasz (HU)

(*) Notice: Subject to any disclaimer, the term of this patent is extended or adjusted under 35 U.S.C. 154(b) by 143 days.

(21) Appl. No.: 15/736,954

(22) PCT Filed: Jun. 27, 2016

(86) PCT No.: PCT/HU2016/050027
§ 371 (c)(1),
(2) Date: Dec. 15, 2017

(87) PCT Pub. No.: WO2017/001876
PCT Pub. Date: Jan. 5, 2017

(65) Prior Publication Data
US 2018/0193187 A1    Jul. 12, 2018

(30) Foreign Application Priority Data

Jun. 29, 2015 (HU) .................... P1500302
Dec. 16, 2015 (HU) .................... P1500621

(51) Int. Cl.
A61F 9/008 (2006.01)
A61N 5/06 (2006.01)
A61B 18/22 (2006.01)
A61N 5/067 (2006.01)

(52) U.S. Cl.
CPC ............ *A61F 9/008* (2013.01); *A61N 5/0613* (2013.01); *A61B 2018/2261* (2013.01); *A61F 2009/00863* (2013.01); *A61N 2005/067* (2013.01); *A61N 2005/0632* (2013.01); *A61N 2005/0644* (2013.01); *A61N 2005/0659* (2013.01)

(58) Field of Classification Search
CPC .. A61B 2018/2261; A61B 18/20–18/28; A61F 2009/00863; A61F 9/008–2009/00897; A61N 2005/0632; A61N 2005/0644; A61N 2005/0659; A61N 2005/067; A61N 5/0613; A61N 5/06–2005/073
USPC ............................................. 606/4–6, 10–12
See application file for complete search history.

(56) References Cited

U.S. PATENT DOCUMENTS

| | | | | |
|---|---|---|---|---|
| 4,866,243 A * | 9/1989 | Sakane | ................... | A61F 9/008 219/121.62 |
| 6,212,012 B1 * | 4/2001 | Tanaka | ............... | B23K 26/0738 359/619 |
| 6,319,273 B1 * | 11/2001 | Chen | ....................... | A61P 27/00 607/88 |
| 2005/0159793 A1 * | 7/2005 | Streeter | .................... | A61H 5/00 607/86 |

(Continued)

*Primary Examiner* — Jonathan T Kuo
(74) *Attorney, Agent, or Firm* — Handal & Morofsky LLC; Anthony H. Handal; Izick Vizel

(57) ABSTRACT

Low power light therapy device for treating the eye, comprising a light source emitting monochromatic or quasi monochromatic light in a wavelength range between 600-700 nm and/or 780-950 nm, and the device comprises a beam expander (2) positioned in the path of the light emitted from the light source and at least one light scattering element (3) arranged past the beam expander (2) and the light intensity at the site of the treatment is smaller than 1 $mW/cm^2$, which is substantially smaller than the output intensity of the light source.

12 Claims, 2 Drawing Sheets

(56) References Cited

U.S. PATENT DOCUMENTS

2009/0216299 A1\* 8/2009 Dantus ................ A61N 5/0616
607/89
2012/0310309 A1\* 12/2012 Shanks ............... A61N 5/0613
607/89

\* cited by examiner

LOW POWER LIGHT THERAPY DEVICE FOR TREATING THE EYE

The invention relates to a low power light therapy device for treating the eye.

The healing effect of low power lasers is widely known. In 1970 Professor Mester, Endre has discovered that hardly healing wounds or those which did not heal at all started to heal under the irradiation with low intensity (soft) laser light. The phenomenon was called biostimulation. Lasers emit monochromatic, coherent polarized light with parallel beams. The biostimulating effect can be attributed to the small bandwidth of the light, to its wavelength (colour), its coherence and polarized nature.

At the same time treatments with parallel beams can be uncomfortable and disadvantageous in certain fields of applications. The summary of such research is included in the article of Mester, E, A. F. and Mester A. "The biomedical effects of laser applications" (Lasers Surg. Med 5, 1985, pp 31-39).

The pioneer work of professor Mester was followed with a high number of researches and the related literature is so rich that one can hardly have a full overview about it. One of the most detailed and comprehensive work is provided in the book of Lars Hode & Jan Tunér: *Laser Phototherapy— Clinical Practice and Scientific Background* (published by Prima Books, Coeymans Hollow, N.Y. USA enlarged edition 2015). In these publications the main attention is directed to the therapeutic applications of low power laser light.

The biostimulation effect of light (not only limited to laser light) is described in detail in the study of professor Michael R. Hamblin (Department of Dermatology, Harvard Medical School, BAR 414, Wellman Center for Photomedicine, Massachusetts General hospital): "Mechanisms of Low Level Light Therapy" published on Aug. 14, 2008 which can be read among other things at the web address: photobiology.info/Hamblin. Chapter 7 of this publication deals whith issues that have yet to be solved, and here he analyzed which properties a light are responsible for the biostimulation effect, i.e. its spectral distribution, monochromatic nature, polarization, its power density or its pulsated application, or the appropriate combination of these properties.

For the biostimulating treatment of the eye with lasers there are no widely accepted methods, but several suggestions have been made for this purpose. It should be noted that here low level (with other words: soft laser) treatments are considered, because the surgical treatment of the eye by lasers cannot be regarded as biostimulation, since then the laser acts on the tissues in an invasive way, namely it destroy the tissues at small spots.

The publication US2005/0159793A1 did not go further than the recognition of the problem, and the only statement is contained therein stating that for the biostimulation of the eye "an efficient electromagnetic radiation should be used that falls in the visible wavelength range". The publication suggests the usable power density range to be between 0.01 mW/cm$^2$ and 100 mW/cm$^2$, whereas it did not give any example how and by devices with what optical properties should such treatments be carried out, and by what extent will the optical properties of the eye lens influence the treatments if carried out by devices considered to be efficient.

A few years later a much more detailed article was published in the periodical: Photomedicine and Laser Surgery, Volume 26, Number 3, 2008 on pp. 241-245 by B. T. Ivandic és Z Ivandic: Low-Level Laser Therapy Improves Vision in Patients with Age-Related Macular Degeneration".

In this paper a laser light source was used with a wavelength of 780 nm having a power of 7.5 mW and a beam diameter of 3 mm. This light was applied obliquely through the cornea in daily four sessions with an energy of 0.3 J per session. The article deals with the beam attenuation effect of the eye, and as a result only a small fraction of the irradiating light will reach the retina. The article failed to disclose the size of the light spot on the retina when the treatment was applied, and the way how the device was oriented during use. The oblique light beams could arrive at the retina only after having passed through the non-transparent tissues of the eye, and it can be supposed that the passage of the light through diffuse tissues its properties (i.e. its polarized nature) have changed or ceased to exist.

A detailed description for the laser therapy of the eye can be read in U.S. Pat. No. 8,105,312, in which the irradiation is carried out through a beam splitter under the inspection of an ophthalmologist. The patent suggests that the treatment is efficient only using a laser light with a wavelength range of 1260 to 1270 nm and suggested the power of the light source to be between 1 mW and 1 W.

The consequences of the focusing effects of the human eye are described in HU P121188, according to which even in case of using a light source of very small power the eye lens focuses the incident light into a very small spot, and as a result a very high power density will appear on the retina where the light is focused, and this high density cause damages there. Therefore the publication suggests the use of diverging lenses arranged in the light path between the light source and the eye, and as a result the afore described power concentration cannot take place and measured on the retina the power density will be decreased to about the $\frac{1}{30}^{th}$ part of the previous value. Starting from the known principles the publication suggests the use of a polarized light source (i. e. it does not limit the light sources to lasers). The publication does not provide any therapeutic example and does not disclose the properties of the device suggested.

For designating "low power laser therapy" a plurality of internationally accepted terms are known, e.g. "Soft Laser Therapy" or "Low Level Laser Therapy, in abbreviation LLPT or "Low Power Laser Therapy", in abbreviation LPLT. A common feature of such lasers is that their power density is sufficiently low not to be able to cause irreversible changes in the treated tissues or to damage their functioning. This statement is correct in case of widely used therapies, however, in case the eye is irradiated through the pupil opening by such a "low" power, then owing to the focusing effect of the eye lens the incident parallel beams will be focused into a small area causing there a high local power density that can damage the tissues in the spot. Therefore the low level laser therapy devices used for treating macular degeneration can have effect only through damaging locally the tissues, i.e. they try to "localize" thereby the degeneration. Owing to the damaging effect laser treatments should be used with utmost care, therefore such treatments could not obtain a wide range of acceptance and use.

The basic task of the invention is to provide a low power light therapy device which can eliminate the described drawbacks and which is capable of realizing the effects of biostimulation known at other part of the organization also in case of the eye.

The invention is based on the discovery that the use of a diffuse power density at most 0.1 mW/cm$^2$ and preferably between 0.06 0.003 mW/cm$^2$ which is substantially smaller than the power used generally in low power laser therapy devices a definite and detectable biostimulating effect will take place in the eye causing so far never experienced therapeutic results, especially but not limited to if the wavelength of the irradiating light is between 600-700 nm and/or 780-900 nm, and if the spectral wavelength range of the irradiating monochromatic light (in case of lasers) or quasi monochromatic light sources is not wider than 20-30 nm, as it is the case with LED light sources. This power density should be interpreted at the outer surface where the light reaches first the eye.

The treatment will be efficient if the size of the therapeutic light spot covers the full area of the eye, i.e. in case a circular light spot it has a diameter of at least 20-25 mm.

Because most light sources emit predominantly parallel beams, then the intentional diffuse effect can be reached more conveniently by the positioning of a light scattering and preferably a light expanding device in the light path of the light source.

It is preferred if the properties of the light scattering elements are chosen in such a way to provide at the same time the required attenuation, because the light output of most light sources is substantially higher than the required power.

A further advantage is obtained if the beam expander provides a certain degree of dispersion of the outgoing light, therefore on its outer surface the arrangement of an optical grid (raster) or small lenses placed at the corner points of the grid.

The surface of the beam expander facing the light source is preferably arranged as a concave lens.

In view of the beam expansion it is preferred if the light scattering element is realized by two spaced elements, in which the element arranged further away from the light source has a greater size corresponding to the expansion of the light beam.

In that case the first light scattering element should provide the higher attenuation.

In case the light source is a laser, then in a preferred embodiment in front of the light scattering element a polarizer sheet is arranged, which ensures that the light which has lost its polarized nature when passing through the light scattering element can regain it by the effect of the polarizer.

The use of polarized light is mostly required if the light source is not a monochromatic type (like a LED source) because the light should be at least either monochromatic or polarized to have a therapeutic effect.

The required power density can be ensured by the appropriate constructional design, but if there is a need to the adjustment of outgoing light in the embodiments using a polarizer this adjustment can be realized by placing a second polarizer sheet in the light path, and the intensity is adjusted if the two polarizers are turned relative to each other. Of course the electronic adjustment of the power of the light source constitutes an alternative way.

In the different embodiments of the invention the light that has the afore defined properties can be monochromatic and not polarized, or monochromatic and polarized, and quasi monochromatic and polarized. These different embodiments have different biostimulating effects and should be chosen according to the intended use.

It should be noted that the most economic solution is if the size of the outgoing light spot when reaching the eye will be only slightly larger than the area of the eye, but in that case the outer surface of the device should be positioned to a distance from the eye shorter than the focal length of the eye (e.g. closer than 15 mm). In this case the eye will be unable to focus even in the slightest extent the incident scattered light and the density of the incident light will be substantially homogenous everywhere.

If this last condition is not kept, then the device can be positioned in a higher distance from the eye, but in that case the outgoing light output should be increased as a quadratic function of the distance from the eye so that the original power density at the eye surface can be attained.

Up to the present if has not been sufficient time to learn and experience all preferred therapeutic properties of the device according to the invention but the examples and results reported in the present specification demonstrate the beneficial and surprising biostimulation and therapeutic effects of the device on the eye, and it can be supposed that the scale of such therapeutic effects will broaden in time.

The invention will now be described in connection with preferable embodiments in which reference will be made to the accompanying drawings. In the drawing.

Figure 1:
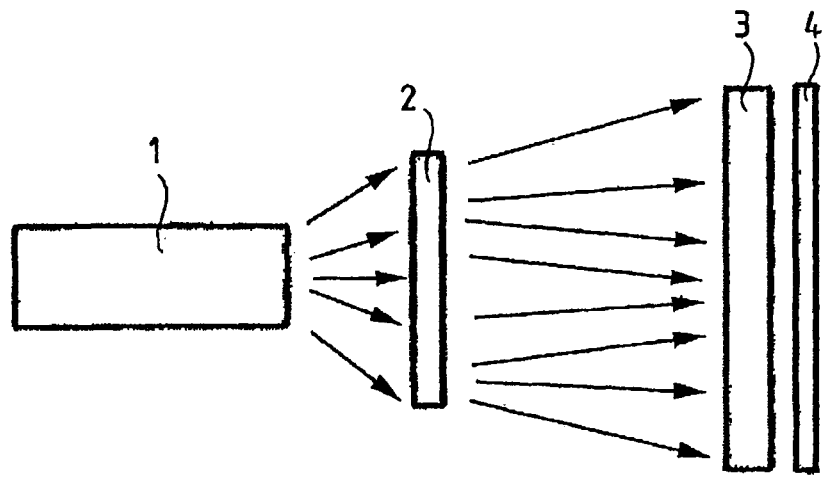
FIG. 1 is a simplified sketch of the device according to the invention.

In FIG. 1 a light source is shown which is a low power base laser 1 used generally for therapy purposes. According to our experiences it is preferred if the wavelength of the light of the base laser 1 falls in the visible range, because in that case we can see during the treatment that the laser is functioning. In the path of the monochromatic, coherent, polarized and parallel light beams that leave the base laser 1 a beam expander 2 (e.g. a concave lens) is arranged from which diverging i.e. non-parallel beams proceed in forward direction. In a predetermined distance from the beam expander 2 a light scattering element 3 is arranged, and the direction of the scattered light leaving the element 3 varies within a broad angular range. The presence of the beam expander 2 and the light scattering element 3 does not change the coherent nature of the light, however, the presence of the light scattering element 3 terminates the polarized nature of the outgoing light, therefore if polarized light is required for the treatment, then a polarizer 4 is arranged in the light path. It should be noted that in certain therapies the presence of the polarizer 4 is not always necessary because monochromatic coherent light can also have a preferred biostimulating effect on the human eye. The area of the outgoing light spot should be chosen so that it illuminates the whole eye or a significant part thereof.

Figure 2:
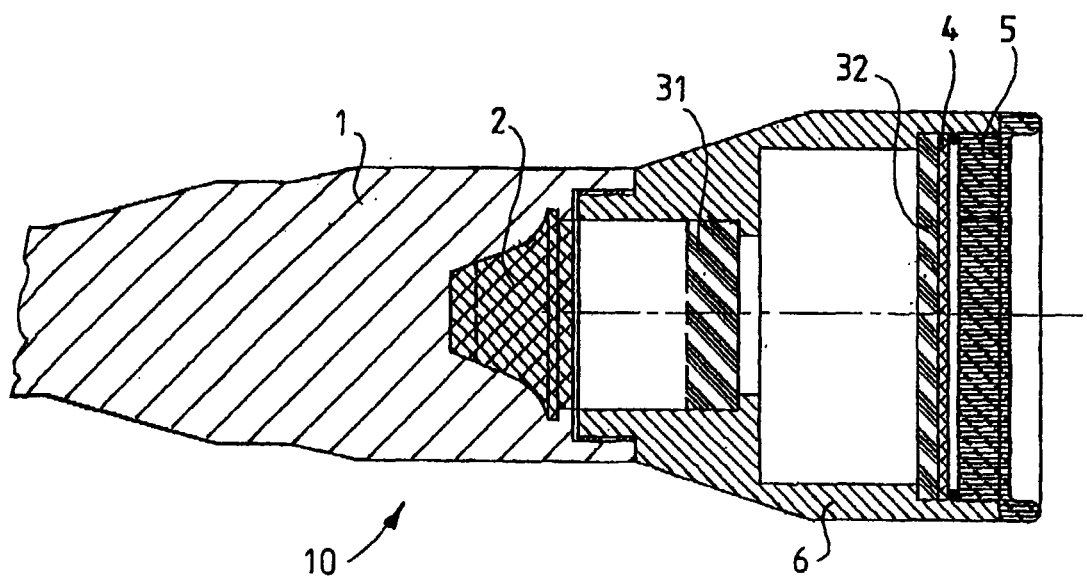
FIG. 2 is a sectional view of a preferred embodiment.
Figure 3:
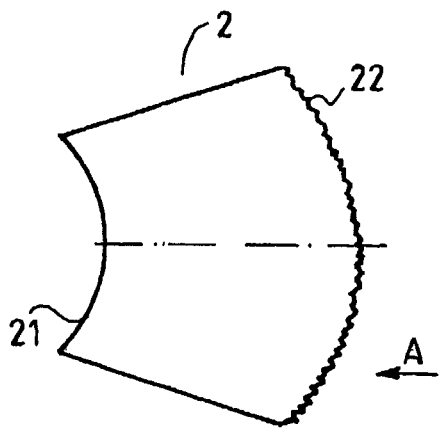
FIG. 3 is the side view of a preferred embodiment of the beam expander 2.
Figure 4:
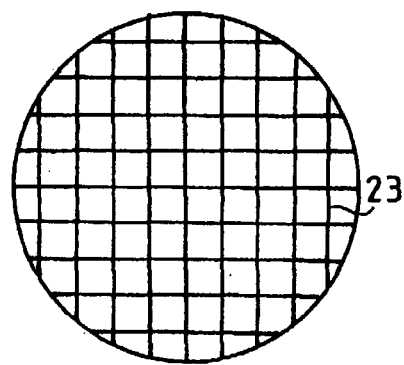
FIG. 4 is the front view of the beam expander shown in FIG. 3.

FIG. 2 shows a preferred embodiment of the device 10 shown in FIG. 1. Identical reference numerals designate identical elements. In FIG. 2 it can be observed that the beam expander 2 has a predetermined length along the light path, and its inlet cross section is smaller than the outlet cross section. FIGS. 3 and 4 show a preferable embodiment of the beam expander 2. The beam expander 2 has a concave inner surface 21 facing towards the base laser 1 and it has a diameter larger that the diameter of the incident light beam. If the light beam has a diameter of e.g. 0.8 mm, than the diameter of the concave inner surface 21 can be about 8 mm. The beam expander 2 has an outwardly expanding conical body and has an outer surface 22 which is provided by a raster 23 of grooves or small spherical lenses arranged at the corner points of the raster 23. In the exemplary embodiment the diameter of the outer surface 22 is preferably 22 mm i.e. nearly the triple of the inner surface 21. The outer surface 22 need not be convex as shown it can have a planar surface as well. FIG. 4 is a view taken from the direction of arrow A in FIG. 3 in which the raster 23 can be observed. The task of the raster 23 has the task to cause an even expansion of the outgoing light beams. The material of the beam expander 2 is transparent plastic or glass.

Reference is made again to FIG. 2, and along the light path in outward direction two light scattering elements 31 and 32 are arranged spaced from the beam expander 2. By adjusting their spacing the diameter of the outgoing light spot can be adjusted. In the exemplary embodiment the diameter of the first light scattering element 31 is also around 22 mm, and its material is a light transparent white porous polyethylene that scatters and homogenizes light that passes through it. In the exemplary embodiment the thickness of the first light scattering element is 8 mm, and it has a light transmission coefficient of 1%. This means that the outgoing light power is around 1.5 mW if the power of the base laser is around 150 mW. The material of the second light scattering element 32 is the same, but it is substantially thinner and its diameter is higher. In the exemplary embodiment the open diameter is 33 mm. The polarizer 4 is arranged in front of the second light scattering element 32, and it has a light transmission coefficient of about 40%. The device 10 has a housing 6 that has a front part that conically widens in forward direction and has an interior designed as shown in FIG. 2. In the housing 6 flanged and threaded connection element and sealing are provided, not shown in the drawing that make possible assembly and disassembly and provide a stable connection to the front part of the base laser 1.

In front of the polarizer 4 a transparent closing plate 5 is provided that closes the internal cavity of the housing and allows passage of the outgoing light beam which has a diameter around 33 mm. In the exemplary embodiment the power density of the outgoing light is 0.05 mW/cm$^2$ which means that the full outgoing power is around 0.43 mW. With such an increased light intensity the adjustment of the intensity of the outgoing light might not be necessary.

Figure 5:
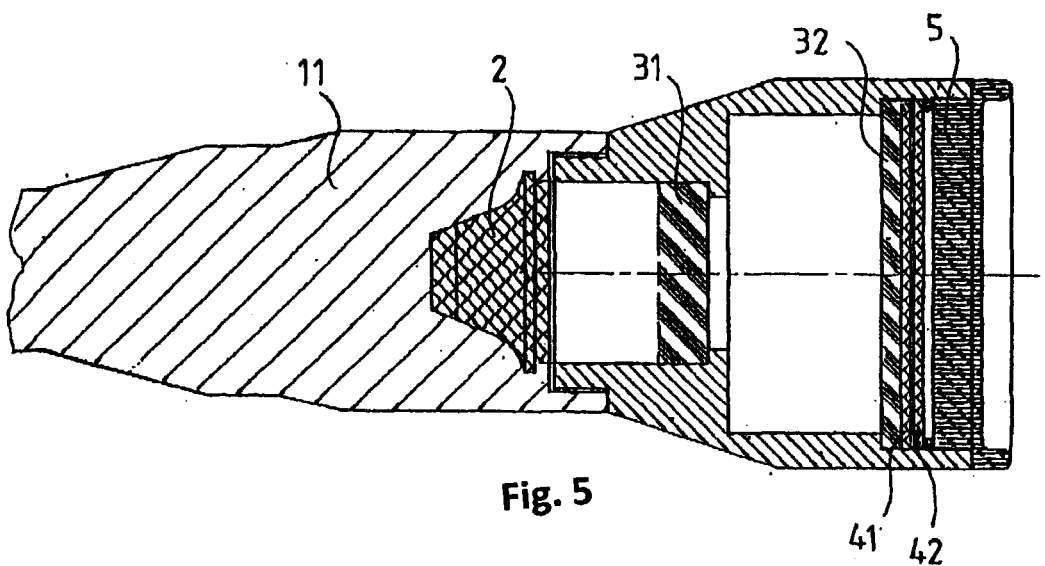
FIG. 5 is similar to FIG. 2 with allowing the adjustment of the outgoing light intensity.

In case such an adjustment was still required, then the embodiment shown in FIG. 5 can be used. This embodiment differs from that shown in FIG. 2 in that behind each other two polarizers 41 and 42 are used, and one of them can be turned around from outside. As it is known a polarizer allows passage of light which has the same polarity, therefore if the two polarizers 41, 42 have the same polarization, they let light pass therethrough (in such case the transmission rate of the polarizers is around 90% but if they are angularly turned with respect to each other, the amount of light that can pass through them gradually decreases, and in case of an angle of 90° no light can pass through, i.e. with this adjustments the outgoing light intensity can be fully decreased.

In case no polarizer 4 is used, i.e. the device 10 generates scattered monochromatic coherent light, then the output intensity can be adjusted by other known ways, i.e. by electronically or optically adjusting the output of the light source in case there is a need at all for such an adjustment.

In a further preferred embodiment of the device 10 instead of the base laser 1 a quasi-monochromatic light source is used issuing light in the required spectral range, and the light intensity is adjusted to fall in the aforementioned preferred range. LED light sources generate light in such a narrow spectral range. For the sake of illustration in FIG. 5 such a quasi monochromatic light source 11 was shown. It should be noted if a plurality of LED sources are used and arranged along a surface substantially equal to that of the polarizers 41, 42, then the role of the beam expander can be substituted by the assembly holding the LED sources from which the light of the LED sources proceed in a large area in forward direction and can directly reach the light scattering elements 31, 32 which homogenize the incident light. In such applications the use of a polarizer 4 is required.

Figure 6:
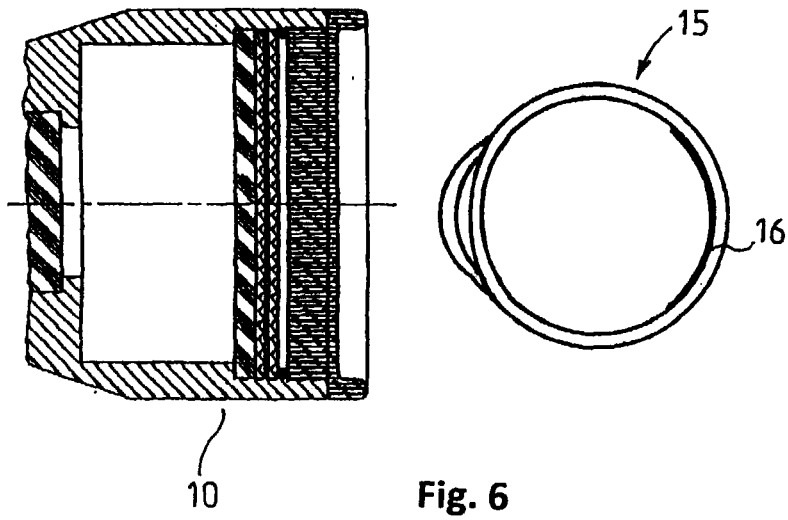
FIG. 6 is a sketch illustrating a preferred way of use of the device.

Reference s made now to FIG. 6 which shows only the front part of the device 10 and in front of it the eye 15 to be treated is shown. It is recommended to keep the distance between the front plane of the device 10 and the eye in a distance smaller than the focal distance of the eye 15, which is preferably between about 7 and 15 mm, because in such a small distance the eye 15 cannot focus the otherwise scattered light, therefore a substantially uniformly distributed light will reach the retina 16 and covers its full area. For the treatment generally there is no need to a dilation of the pupil.

The device 10 according to the invention has beneficial effect not only on the retina as it penetrates to all tissues in the eye and behind the retina and has an effect on the physiologic processes therein.

If light fall on the front surface of the eye 15 with a power intensity of 0.05 mW/cm$^2$, then the retina will receive about $\frac{1}{5}^{th}$ part, therefore the density there will be around 0.01 MW/cm$^2$. This value has been obtained from measurements of pig's eyes.

Naturally treatment can be made also from higher distances, but in this case the distance should be at least ten times as high as the focal distance of the eye, In that case the area of the light spot should be chosen so that the spot covers the hole area of the eye. Depending on the size of the incident light spot and on the distance the light intensity should be increased to such an extent that the light received by the eye should be in the efficient range.

The range of light intensity used for therapy should be chosen so that it cannot disturb or be inconvenient for the patient. Because the eye can adapt to a very large range of light intensities, since in dark even the light of a remotely located candle can be seen, and in summer one can watch the blue sky without feeling any inconvenience. Therefore one has to be rather cautious in drawing the limits of the applicable range. It has been experienced that most people do not feel inconvenient an incident light intensity of 1 mW/cm$^2$, and this especially true for subjects having a decreased vision as a result of a disease or macular degeneration. Because the light intensity used by the device 10 is about the twentieth portion of this value, it can be assumed that the upper limit of the applicable range could be around this 1 mW/cm$^2$. Owing to the scattered nature of the incident light with such intensity no damage can be caused at any part of the eye. A similar uncertainty concerns the lower limit, because the sensitivity of different eye tissues can be very different. Even because the incredible sensitivity of human eye no lower limit can be defined, especially because the light energy provided during a treatment is the product of the power intensity and the duration time of the treatment, thus a decrease in intensity can be compensated by an increased duration.

The potential therapeutic uses of the device 10 according to the invention are very high and not yet fully tried and they affect most known eye problems. The pertinent literature has demonstrated that light therapy has a wide range of effects on the living tissues.

In the following a few examples will be provided which support the many advantages of the device according to the invention.

EXAMPLE 1

H. E. is a female patient aged 64 who had glaucoma on both eyes for a long time.

With medicaments (Xalaton) her eye pressure could be kept between 21 and 19 Hgmm values.

When she gave up using the medicament and received a polarized scattered laser light treatment in the aforementioned intensity having a wavelength of 660 nm for the duration of daily 5 minutes, her eye pressure dropped after a month treatment to 12-14 Hgmm.

Here ophthalmologist considered this as an unbelievably good result.

EXAMPLE 2

E.K. is a male patient aged 70 and he had a definite presbyopia. Using the device an treatment as described in Example 1 the following results were experienced:

After a treatment of 1 month his vision improved by 1 diopter. After 2 months of treatment the improvement was 2 diopter, and in the third months he reported a further gradual improvement.

EXAMPLE 3

M.H. Zs is a female patient aged 54. She had a blurred vision following a surgery of astigmatism. With one of her eyes she cannot practically see anything, and this eye was treated only.

At the starting stage she could not see the numbers on a Snellen chart. After 5 days of treatment, she could see the first line of the Snellen chart. Following the 2 nd week she could see the second line of the chart. After 3 weeks of treatment her astigmatic eye has taken normal position several times a day. After the eleventh week she saw the $3^{rd}$ line on the Snellen chart.

EXAMPLE 4

B. J. O is a female patient aged 87 years. In the initial state she was practically blind because of macular degeneration, in her room she can move only when she is led by her hands. She cannot see her finger when she extends the arm. Her treatment took place as in the foregoing examples.

After a 1 month treatment the impermeable white fog started to dissolve.

After two months of treatment the fog has become more diluted, the sensible distance increased to a range between 1 and 2 meters. With time the foggy periods have become shorter.

After the third month the fog diluted and has become more transparent. She experienced periods with sharper sight. She started recognizing objects in her room, moved without assistance and could care for herself. Her back become more upright as she did not need to lean forward to recognize objects. She started sensing colours.

EXAMPLE 5

In this example an animal was treated with the device in a similar way. The animal was a 7 years old dog who lost its sight as a consequence of Lyme disease due to *Borelia afzelii* infection. The antibiotic treatments brought no result, and doctors were thinking on its euthanasia.

In a few weeks of laser treatment and the addition of methylene blue the inflammation ceased to exist and the dog has regained its vision.

The examples shown have demonstrated that the device according to the invention has a detectable beneficial effect not only on macular degeneration but practically on all functions of the eye. The underlying reasons cannot be known for the time being, but in case of macular degeneration it is rather likely that the treatment acts not only on the retina itself but the scattered laser light in the chosen range of wavelength penetrates deeply in the tissues behind the retina, and the blood supply, circulation and biological function of these tissues can be important from the point of view of vision.

The device 10 according to the invention has been shown in its most simple embodiment, and in the practice it might be worthwhile to use a pair of such devices mechanically connected to each other similar to the design of binoculars, wherein the distance between the two devices can be adjusted like in case of binoculars, whereby both eyes can be treated at the same time, that can halve the full duration of treatment. In case of professional designs the device can be assembled on a stander provided both with a chin and forehead support, whereby a fixed treatment means is obtained which is similar to other devices used in ophthalmic examinations in which the head is positioned in a stable way in the device.

Without departure from the basic concept of the invention several other structural realizations can be made, e.g. for expanding and homogenizing the beams leaving the light source there are several other known ways different from those shown in the examples.

The invention claimed is:

1. Low power light therapy device for treating the eye, comprising:
    a light source emitting monochromatic or quasi monochromatic light in a wavelength range between 600 700 nm and/or 780-950 nm,
    a beam expander positioned in the path of the light emitted from the light source for producing wider outgoing beams, wherein the beam expander has a concave inner surface and an outer surface provided by a raster of small lenses,
    at least one light scattering element arranged passed the beam expander across the path of the wider beams and the light intensity at a site of treatment is smaller than 1 mW/cm$^2$, which is substantially smaller than the output intensity of the light source
    a polarizer in the light path leaving the at least one light scattering element.

2. The device as claimed in claim 1, wherein at the site of treatment the light intensity is smaller than 0.1 mW/cm$^2$.

3. The device as claimed in claim 1, wherein the light source is a base laser.

4. The device as claimed in claim 1, wherein the at least one light scattering element comprises two spaced light scattering elements made of a material that homogenizes light that passes therethrough and has a decreased transparence, and the combined attenuation of the light scattering elements substantially corresponds to the attenuation required between the light source and the site of treatment to provide the required light intensity.

5. The device as claimed in claim 1, wherein the at least one light scattering element comprises a first and a second light scattering element wherein the second light scattering element as counted from the light source is thinner than the first light scattering element and has a size larger than that of the first light scattering element.

6. The device as claimed in claim 1, wherein the polarizer comprises a first and second polarizer arranged one after the other, and one of the polarizers can be turned relative to the other polarizer, for adjusting the intensity of the outgoing light.

7. The device as claimed in claim 1, further comprising a circularly symmetric hollow housing adapted to mechanically fix the at least one light scattering elements in the device, and a closing plate arranged to close the front of the hollow opening.

8. The device as claimed in claim 1, wherein the emitted light results in a light spot having a size of the eye or larger.

9. The device as claimed in claim 8, wherein the light spot has a circular shape and a diameter between about 30 and 40 mm.

10. Low power light therapy device for treating the eye, comprising
- a laser light source emitting monochromatic or quasi monochromatic light in a wavelength range between 600-700 nm and/or 780-950 nm,
- a beam expander positioned in the path of the light emitted from the light source,
- at least one light scattering element arranged passed the beam expander providing scattered beams and substantial attenuation,
- and a polarizer inserted in the light path leaving the light scattering element.

11. The device as claimed in claim 10, wherein the polarizer comprises a first and a second separate polarizer arranged one after the other, and one of the separate polarizers can be turned relative to the other one for adjusting the intensity of the outgoing light.

12. The device as claimed in claim 10, wherein the beam expander has a concave inner surface and an outer surface provided by a raster of small lenses.

* * * * *